(12) United States Patent
Shiraishi et al.

(10) Patent No.: US 10,261,034 B2
(45) Date of Patent: Apr. 16, 2019

(54) HEAT FLOW DISTRIBUTION MEASUREMENT DEVICE

(71) Applicant: DENSO CORPORATION, Kariya, Aichi-pref. (JP)

(72) Inventors: Yoshihiko Shiraishi, Kariya (JP); Atusi Sakaida, Kariya (JP); Norio Gouko, Kariya (JP); Toshihisa Taniguchi, Kariya (JP); Keiji Okamoto, Kariya (JP)

(73) Assignee: DENSO CORPORATION, Kariya, Aichi-pref. (JP)

(*) Notice: Subject to any disclaimer, the term of this patent is extended or adjusted under 35 U.S.C. 154(b) by 190 days.

(21) Appl. No.: 15/310,839

(22) PCT Filed: Jun. 1, 2015

(86) PCT No.: PCT/JP2015/002742
§ 371 (c)(1),
(2) Date: Nov. 14, 2016

(87) PCT Pub. No.: WO2015/186330
PCT Pub. Date: Dec. 10, 2015

(65) Prior Publication Data
US 2017/0082564 A1    Mar. 23, 2017

(30) Foreign Application Priority Data

Jun. 3, 2014 (JP) .................................. 2014-114827
May 14, 2015 (JP) .................................. 2015-099314

(51) Int. Cl.
*G01N 25/18* (2006.01)
*G01K 17/00* (2006.01)
(Continued)

(52) U.S. Cl.
CPC ............. *G01N 25/18* (2013.01); *G01K 17/00* (2013.01); *H01L 35/32* (2013.01); *H01L 35/325* (2013.01); *H01L 35/34* (2013.01)

(58) Field of Classification Search
CPC combination set(s) only.
See application file for complete search history.

(56) References Cited

U.S. PATENT DOCUMENTS 5,430,322 A    7/1995 Koyanagi et al.
6,190,040 B1*  2/2001 Renken ................. G01K 1/026
                                                            374/133
(Continued)

FOREIGN PATENT DOCUMENTS

CN    101013715 A    8/2007
CN    101571428 A    11/2009
(Continued)

*Primary Examiner* — Harshad R Patel
*Assistant Examiner* — Nasir U. Ahmed
(74) *Attorney, Agent, or Firm* — Harness, Dickey & Pierce, P.L.C.

(57) ABSTRACT

A heat flow distribution measurement device includes a sensor module having one multilayer substrate and a plurality of heat flow sensor portions arranged inside of the multilayer substrate. The multilayer substrate has one surface and another surface opposite to the one surface and includes a plurality of stacked insulating layers each formed of a thermoplastic resin. The heat flow sensor portions are each formed of thermoelectric conversion elements and are thermoelectrically independent. An arithmetic portion arithmetically determines a heat flow distribution based on an electromotive force generated in each of the heat flow sensor portions. The thermoelectric conversion elements are formed in the multilayer substrate and therefore manufactured by the same manufacturing process for manufacturing the multilayer substrate. This can minimize the performance (Continued)

difference between the individual thermoelectric conversion elements and allow the heat flow distribution to be measured with high precision.

10 Claims, 11 Drawing Sheets

(51) Int. Cl.
*H01L 35/32* (2006.01)
*H01L 35/34* (2006.01)

(56) References Cited

U.S. PATENT DOCUMENTS

| | | | | |
|---|---|---|---|---|
| 6,535,824 | B1* | 3/2003 | Mansky | B01J 19/0046 374/49 |
| 6,991,366 | B2* | 1/2006 | Naka | G01N 25/18 374/137 |
| 2005/0205766 | A1 | 9/2005 | Sawada | |
| 2007/0181650 | A1 | 8/2007 | Yoo et al. | |
| 2010/0158069 | A1* | 6/2010 | Yoo et al. | |
| 2012/0161003 | A1* | 6/2012 | Tsuchiya | G01J 5/0225 250/338.3 |
| 2013/0083821 | A1 | 4/2013 | Schwank et al. | |
| 2013/0193820 | A1* | 8/2013 | Kwon | G01K 17/20 312/236 |
| 2015/0144171 | A1* | 5/2015 | Taniguchi | H01L 23/38 136/205 |

FOREIGN PATENT DOCUMENTS

| | | |
|---|---|---|
| GB | 2502373 A | 11/2013 |
| JP | 2636119 B2 | 7/1997 |
| JP | 2005337739 A | 12/2005 |
| JP | 4595073 B2 | 12/2010 |
| JP | 2011187619 A | 9/2011 |
| JP | 2012255717 A | 12/2012 |
| JP | 2014007376 A | 1/2014 |
| KR | 101012666 B1 | 2/2011 |
| WO | WO-2015186328 A1 | 12/2015 |

* cited by examiner

HEAT FLOW DISTRIBUTION MEASUREMENT DEVICE

CROSS REFERENCE TO RELATED APPLICATIONS

This application is a U.S. National Phase Application under 35 U.S.C. 371 of International Application No. PCT/JP2015/002742 filed on Jun. 1, 2015 and published in Japanese as WO 2015/186330 A1 on Dec. 10, 2015. This application is based on and claims the benefit of priority from Japanese Patent Application No. 2014-114827 filed on Jun. 3, 2014 and Japanese Patent Application No. 2015-099314 filed on May 14, 2015. The entire disclosures of all of the above applications are incorporated herein by reference.

TECHNICAL FIELD

The present disclosure relates to a heat flow distribution measurement device.

BACKGROUND ART

Examples of a heat flow sensor which senses a heat flow include the one described in Patent Literature 1. The heat flow sensor uses a thermoelectric conversion element. Specifically, a plurality of through holes are formed in an insulating base material and first and second conductive metals as different metal materials are embedded in the plurality of through holes and alternately connected in series.

PRIOR ART LITERATURE

Patent Literature

[Patent Literature 1] JP 2012-255717 A

SUMMARY OF INVENTION

For example, there is a case where it is desired to know in what heat energy (heat flow) distribution a given plate-like heater produces heat. Also, there is a case where it is desired to know the heat release distribution of the heat sink provided on a printed circuit board or the like.

In the case where it is desired to measure the heat flow distribution of a measurement target such as a heater or a heat sink, it can be considered to measure the heat flow distribution using a plurality of the heat flow sensors described above. For example, it can be considered to perform the measurement by placing the plurality of heat flow sensors on the surface of an object to be heated away from the measurement target and attach the plurality of heat flow sensors to the measurement target.

However, the plurality of heat flow sensors manufactured as separate and independent bodies have performance differences therebetween, so it has been difficult to measure the heat flow distribution with high precision.

There is also a method which measures a heat flow distribution using a thermographic device. However, what can be measured by thermography is the distribution of a surface temperature determined from infrared wavelengths. Since the distribution of the surface temperature is not a heat flow distribution, to convert the distribution of the surface temperature to a heat flow distribution, it is necessary to perform analysis by taking various elements into account.

Accordingly, by this method also, it is difficult to measure a heat flow distribution with high precision.

An object of the present disclosure is to provide a heat flow distribution measurement device capable of measuring a heat flow distribution with high precision.

According to a first aspect of the present disclosure, a heat flow distribution measurement device includes a sensor module having one multilayer substrate and a plurality of heat flow sensor portions arranged inside of the multilayer substrate. The multilayer substrate has one surface and another surface opposite to the one surface and includes a plurality of stacked insulating layers each formed of a thermoplastic resin. Each of the plurality of heat flow sensor portions is formed of an electrically independent thermoelectric conversion element. When the sensor module is placed with the one surface facing a measurement target of which a heat flow distribution is to be measured, each of the thermoelectric conversion elements produces an electric output in accordance with a heat flow passing through the inside of the multilayer substrate in a direction perpendicular to the one surface.

According to a second aspect of the present disclosure, the heat flow distribution measurement device according to the first aspect further includes an arithmetic portion that arithmetically determines the heat flow distribution on the basis of the electric output produced by each of the plurality of heat flow sensor portions.

In each of the heat flow distribution measurement devices according to the foregoing first and second aspects, the thermoelectric conversion elements forming the respective heat flow sensor portions are formed in the single multilayer substrate and are therefore manufactured by the same manufacturing process for manufacturing the multilayer substrate. This allows the performance difference between the individual thermoelectric conversion elements to be smaller than in the case where a plurality of heat flow sensors are manufactured as separate and independent bodies.

Accordingly, the heat flow distribution can be measured with higher precision than in the case where a heat flow distribution is measured using the plurality of heat flow sensors manufactured as separate and independent bodies.

According to a third aspect of the present disclosure, a heat flow distribution measurement device includes a sensor module having one multilayer substrate and a plurality of heat flow sensor portions arranged inside of the multilayer substrate. The multilayer substrate has one surface and another surface opposite to the one surface and includes a plurality of stacked insulating layers. Each of the plurality of heat flow sensor portions is formed of an electrically independent thermoelectric conversion element. When the sensor module is placed with the one surface facing a measurement target of which a heat flow distribution is to be measured, each of the thermoelectric conversion elements produces an electric output in accordance with a heat flow passing through the inside of the multilayer substrate in a direction extending from one of the one surface and the other surface to the other of the one surface and the other surface.

In the heat flow distribution device according to the third aspect also, for the same reason as given for the heat flow distribution measurement devices according to the first and second aspects, a heat flow distribution can be measured with higher precision than in the case where a heat flow distribution is measured using a plurality of heat flow sensors manufactured as separate and independent bodies.

BRIEF DESCRIPTION OF DRAWINGS

The above and other objects, features and advantages of the present disclosure will become more apparent from the following detailed description made with reference to the accompanying drawings, in which.

DESCRIPTION OF EMBODIMENTS

Figure 1:
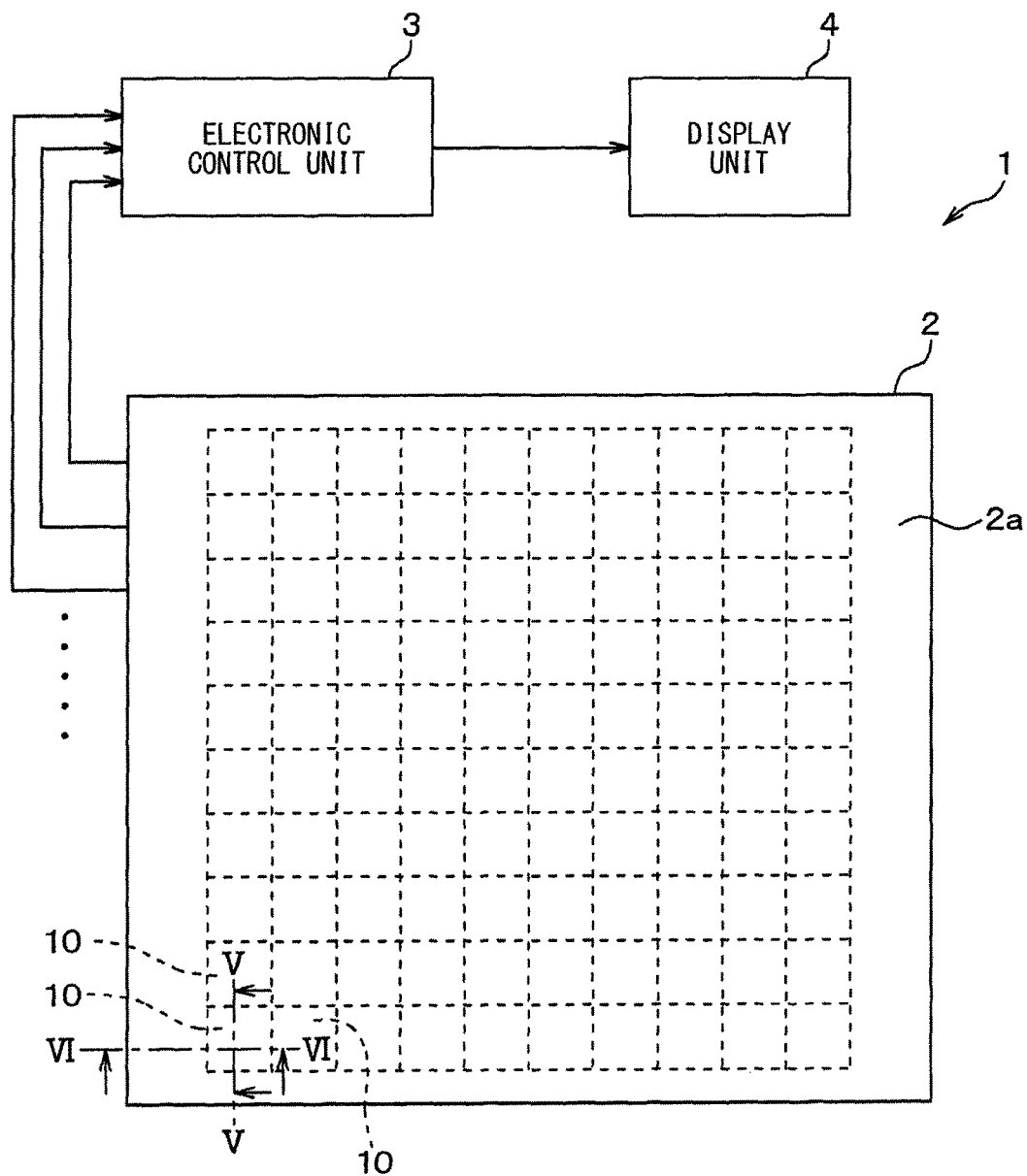
FIG. 1 is a schematic diagram showing a configuration of a heat flow distribution measurement device according to a first embodiment.

The following will describe the embodiments of the present disclosure on the basis of the drawings. In the following description of the different embodiments, like or equivalent component parts are designated by like reference characters or numerals.

First Embodiment

As shown in FIG. 1, a heat flow distribution measurement device 1 of the present embodiment includes a sensor module 2, an electronic control unit 3, and a display unit 4.

The sensor module 2 includes a plurality of integrated heat flow sensor portions 10 each of which measures a heat flow. The sensor module 2 has a flat plate shape having one surface 2a (first surface) and another surface 2b (second surface) opposite thereto (see FIG. 3). In the present embodiment, the heat flow sensor portions 10 are arranged in a matrix configuration in directions parallel with the one surface 2a. Each of the quadrilaterals shown by the broken lines in FIG. 1 shows a portion functioning as one heat flow sensor portion 10. As shown in FIG. 1, each of the plurality of heat flow sensor portions 10 has a length in one direction and a length in another direction perpendicular thereto which are equal to each other. The plurality of heat flow sensor portions 10 are orderly arranged in the one direction and the other direction. The heat flow sensor portions 10 in adjacent rows which face each other are at matching positions.

The plurality of heat flow sensor portions 10 are electrically independent of each other and connected to the electronic control unit 3 via wiring. Note that, as will be described later, the heat flow sensor portions 10 correspond to a region of a multilayer substrate where thermoelectric conversion elements connected in series are formed.

The electronic control unit 3 functions as an arithmetic portion that arithmetically determines a heat flow distribution. The electronic control unit 3 includes, e.g., a microcomputer, a memory as a storage means, and a peripheral circuit thereof and performs a predetermined arithmetic process in accordance with a preset program. The electronic control unit 3 arithmetically determines a heat flow distribution of a measurement target on the basis of the result of the sensing of a heat flow by the plurality of heat flow sensor portions 10 and performs image processing thereon to cause the display unit 4 to display the heat flow distribution as a two-dimensional image.

The display unit 4 displays a two-dimensional image of a heat flow distribution. As the display unit 4, a typical image display unit can be used.

Figure 2:
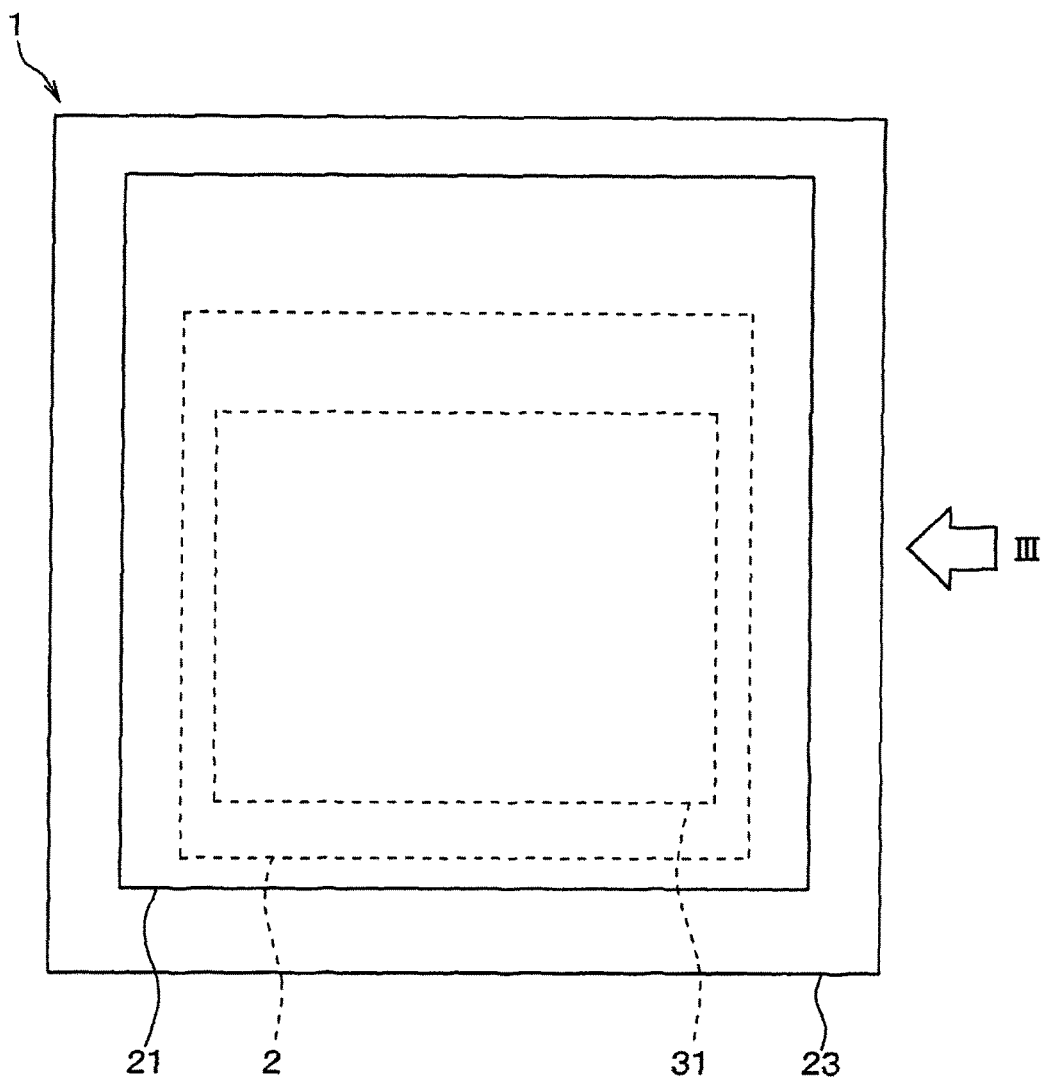
FIG. 2 is a plan view of the heat flow distribution measurement device according to the first embodiment.
Figure 3:
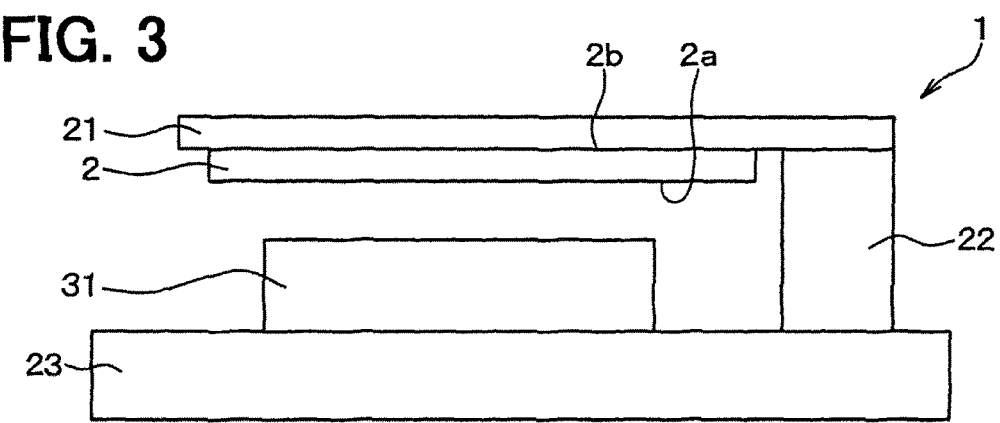
FIG. 3 is a side view of the heat flow distribution measurement device viewed in the direction shown by the arrow III in FIG. 2.

Also, as shown in FIGS. 2 and 3, the heat flow distribution measurement device 1 includes a sensor head 21 on which the sensor module 2 is placed, a support pillar 22 which supports the sensor head 21, and a stage 23 on which a measurement target 31 is placed.

On the lower surface of the sensor head 21, the sensor module 2 is disposed. As a result, the other surface 2b of the sensor module 2 is fixed to the sensor head 21 and the one surface 2a of the sensor module 2 faces the measurement target 31. The support pillar 22 has a mechanism which allows height adjustment so that the distance between the sensor module 2 and the measurement target 31 is adjustable.

Next, a description will be given of a specific structure of the sensor module 2. The sensor module 2 includes the plurality of heat flow sensor portions 10 each having the same internal structure and formed in one multilayer substrate. Therefore, the following will describe the structure of one of the heat flow sensor portions 10.

Figure 4:
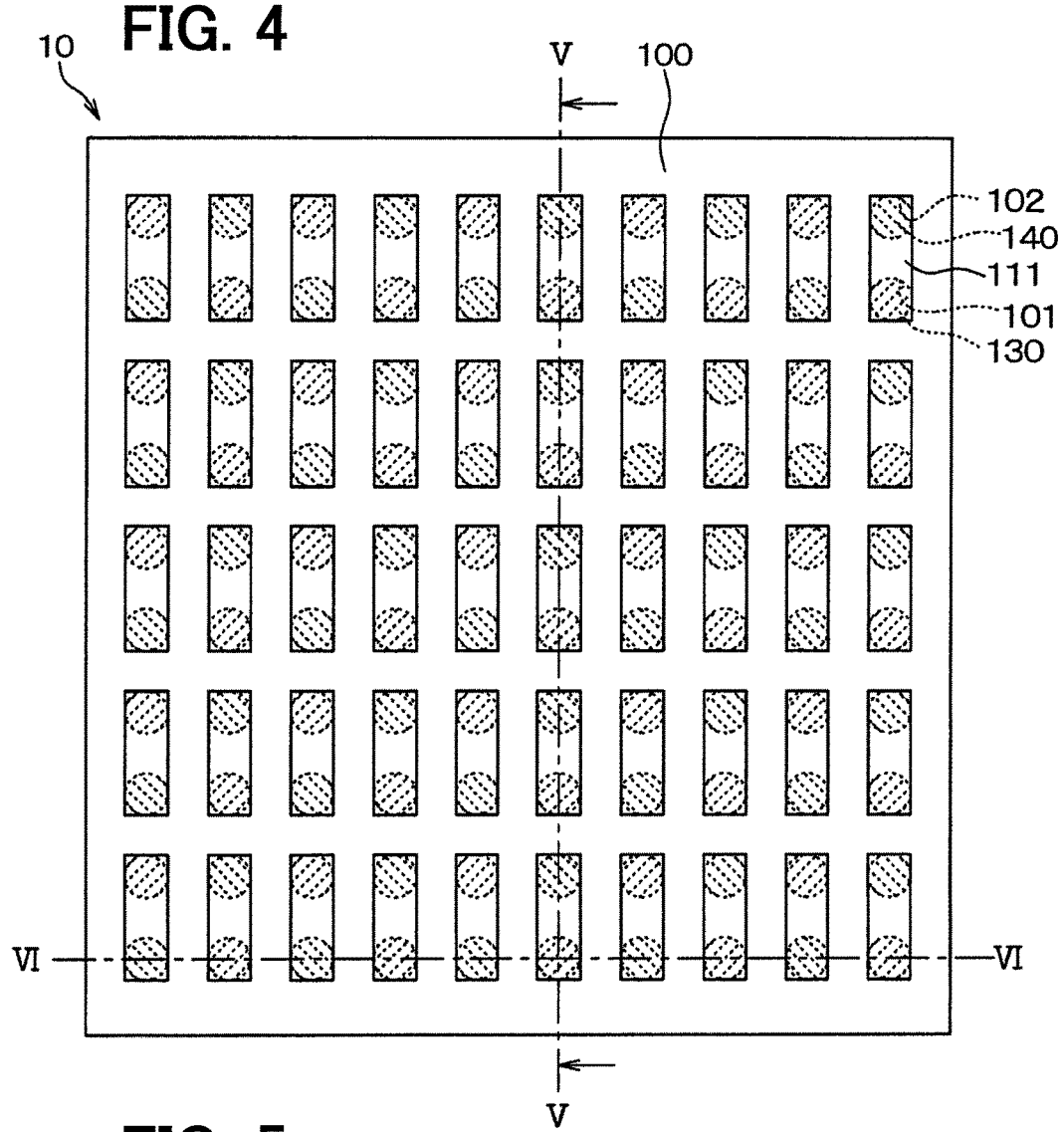
FIG. 4 is a plan view of one of heat flow sensor portions in the sensor module in FIG. 1.
Figure 5:
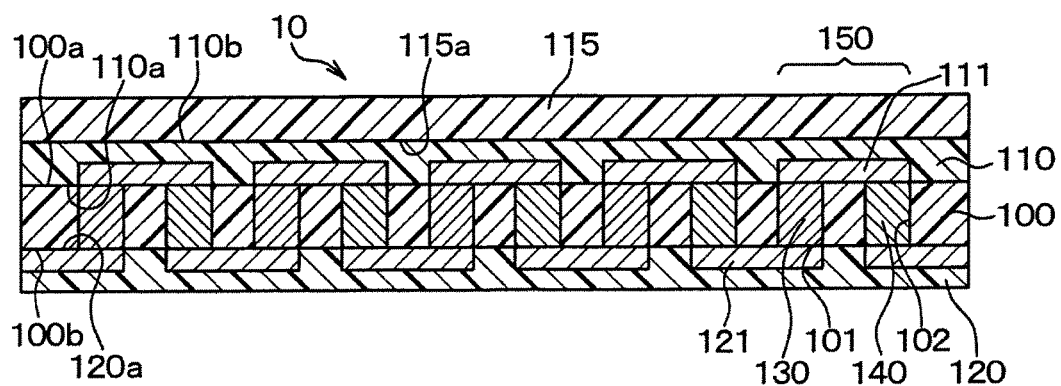
FIG. 5 is a cross-sectional view taken along the line V-V in FIG. 4.
Figure 6:
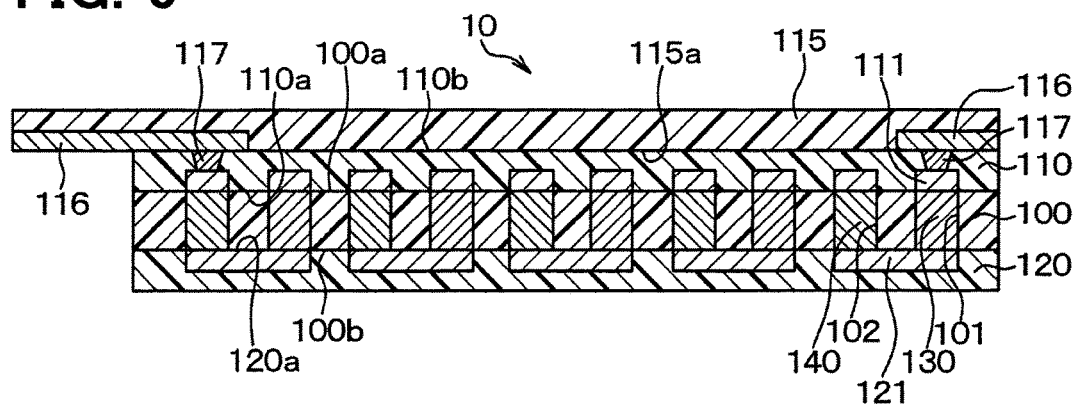
FIG. 6 is a cross-sectional view taken along the line VI-VI in FIG. 4.

As shown in FIGS. 4 to 6, one of the heat flow sensor portions 10 has an insulating base material 100, an insulating layer 110, a surface protection member 115, and a back-surface protection member 120 which are stacked to be integrated. In the integrated stack, first and second interlayer connection members 130 and 140 are alternately connected in series. FIG. 4 is a plan view of each one of the heat flow sensor portions 10 but, for easier understanding, the illustration of the surface protection member 115 and the insulating layer 110 is omitted. Also, FIG. 4 is not a cross-sectional view but, for easier understanding, the first and second interlayer connection members 130 and 140 are hatched.

The insulating base material 100 is formed of a film made of a thermoplastic resin represented by polyetheretherketone (PEEK), polyetherimide (PEI), a liquid crystal polymer (LCP), or the like. The insulating base material 100 is formed in a zigzag pattern such that a plurality of first and second via holes 101 and 102 extending through the insulating base material 100 in a thickness direction are staggered with respect to each other. The first and second via holes 101 and 102 are through holes extending from one surface 100a of the insulating base material 100 to another surface 100b through the insulating base material 100.

Note that each of the first and second via holes 101 and 102 in the present embodiment has a cylindrical shape having a diameter which is uniform in the direction extending from the top surface 100a to the back surface 100b. However, each of the first and second via holes 101 and 102 may have a tapered shape having a diameter which decreases with distance from the top surface 100a toward the back surface 100b. Alternatively, each of the first and second via holes 101 and 102 may have a tapered shape having a diameter which decreases with distance from the back surface 100b toward the top surface 100a or an angular cylindrical shape.

In the first via holes 101, the first interlayer connection members 130 are disposed while, in the second via holes 102, the second interlayer connection members 140 are disposed. That is, in the insulating base material 100, the first and second interlayer connection members 130 and 140 are arranged to be staggered with respect to each other.

Since the first and second interlayer connection members 130 and 140 are thus disposed in the first and second via holes 101 and 102, by appropriately changing the numbers of the first and second via holes 101 and 102, the diameters thereof, the spaces therebetween, or the like, it is possible to increase the density of the first and second interlayer connection members 130 and 140. This can increase the electromotive force generated in the first and second interlayer connection members 130 and 140 alternately arranged in series, i.e., voltage and increase the sensitivity of each of the heat flow sensor portions 10.

The first and second interlayer connection members 130 and 140 are first and second conductors formed of different conductive materials so as to achieve a Seebeck effect. Examples of the conductive materials include a metal and a semiconductor. For example, each of the first interlayer connection members 130 is formed of a metal compound obtained by subjecting a Bi—Sb—Te alloy powder showing a P-type conductivity type to solid-phase sintering such that the plurality of metal atoms retain the crystal structures thereof before the sintering. On the other hand, the second interlayer connection member 140 is formed of a metal compound obtained by subjecting a Bi—Te alloy powder showing an N-type conductivity type to solid-phase sintering such that the plurality of metal atoms retain the crystal structures thereof before the sintering. Thus, the metals forming the first and second interlayer connection members 130 and 140 are sintered alloys obtained by sintering the plurality of metal atoms in the state where the metal atoms retain the crystal structures thereof. This can increase the electromotive force generated in each of the first and second interlayer connection members 130 and 140 alternately arranged in series and increase the sensitivity of each of the heat flow sensor portions 10.

On the top surface 100a of the insulating base material 100, the insulating layer 110 is disposed. The insulating layer 110 is formed of a film made of a thermoplastic resin represented by polyetheretherketone (PEEK), a polyetherimide (PEI), a liquid crystal polymer (LCP), or the like. In the one surface 110a of the insulating layer 110 which faces the insulating base material 100, a plurality of top-surface patterns 111 resulting from the patterning of a copper foil or the like are formed so as to be spaced apart from each other. Each of the top-surface patterns 111 is electrically connected appropriately to the first and second interlayer connection members 130 and 140.

Specifically, when it is assumed that one of the first interlayer connection members 130 and one of the second interlayer connection members 140 which are adjacent to each other form one pair 150 as shown in FIG. 5, the first and second interlayer connection members 130 and 140 in each one of the pairs 150 are connected to the same top-surface pattern 111. That is, the first and second interlayer connection members 130 and 140 in each one of the pairs 150 are electrically connected via the top-surface pattern 111. Note that, in the present embodiment, one of the first interlayer connection members 130 and one of the second interlayer connection members 140 which are adjacent to each other along one direction (a left and right direction in FIG. 5) form one of the pairs 150.

On the back surface 110b of the insulating base material 100, the back-surface protection member 120 is disposed. The back-surface protection member 120 is formed of a film made of a thermoplastic resin represented by polyetheretherketone (PEEK), polyetherimide (PEI), a liquid crystal polymer (LCP), or the like. In the one surface 120a of the back-surface protection member 120 which faces the insulating base material 100, a plurality of back-surface patterns 121 resulting from the patterning of a copper foil or the like are formed so as to be spaced apart from each other. Each of the back-surface patterns 121 is electrically connected appropriately to the first and second interlayer connection members 130 and 140.

Specifically, as shown in FIG. 5, the first interlayer connection member 130 in one of the two pairs 150 adjacent to each other in one direction and the second interlayer connection member 140 in the other of the two pairs 150 are connected to the same back-surface pattern 121. That is, the first and second interlayer connection members 130 and 140 respectively belonging to one and the other of the different pairs 150 are electrically connected via the same back-surface pattern 121.

Also, as shown in FIG. 6, in the end portion of one of the heat flow sensor portions 10, the first and second interlayer connection members 130 and 140 adjacent to each other along another direction (left-right direction over the surface of the paper sheet with FIG. 4 or FIG. 6) orthogonal to the one direction are connected to the same back-surface pattern 121.

Thus, the individual pairs 150 are connected in series and arranged in the multilayer substrate such that a sequence of the pairs 150 connected in one direction (an up and down direction in FIG. 4) is repeatedly bent back. Note that one pair of the first and second interlayer connection members 130 and 140 connected to each other form one thermoelectric conversion element. Accordingly, each one of the plurality of heat flow sensor portions 10 includes the plurality of thermoelectric conversion elements connected in series. Note that the plurality of heat flow sensor portions 10 are electrically independent of each other and each one of the plurality of heat flow sensor portions 10 is electrically connected individually to the electronic control unit 3. In the present description, the plurality of thermoelectric conversion elements electrically connected in series to form each one of the heat flow sensor portions 10 are referred to as an electrically independent thermoelectric conversion element.

On the other surface 110b of the insulating layer 110, the surface protection member 115 is disposed. The surface protection member 115 is formed of a film made of a thermoplastic resin represented by polyetheretherketone (PEEK), polyetherimide (PEI), a liquid crystal polymer (LCP), or the like. As shown in FIG. 6, in the one surface 115a of the surface protection member 115 which faces the insulating layer 110, a plurality of wiring patterns 116 resulting from the patterning of a copper foil or the like are formed. In each one of the heat flow sensor portions 10, the wiring patterns 116 are electrically connected to the end portions of the first and second interlayer connection members 130 and 140 connected in series as described above via an interlayer connection member 117 formed in the insulating layer 110.

Figure 7:
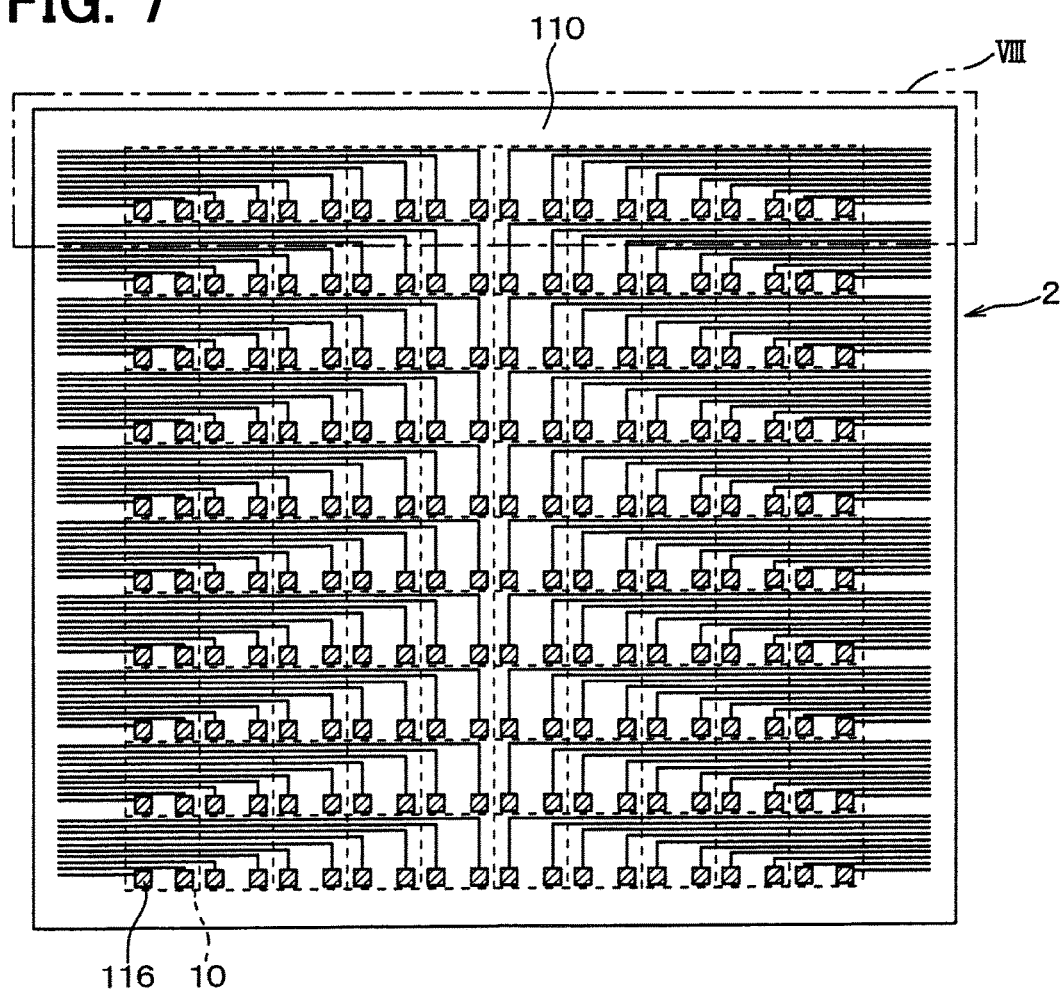
FIG. 7 is a plan view from which a surface protection member of the sensor module in FIG. 1 has been omitted.
Figure 8:
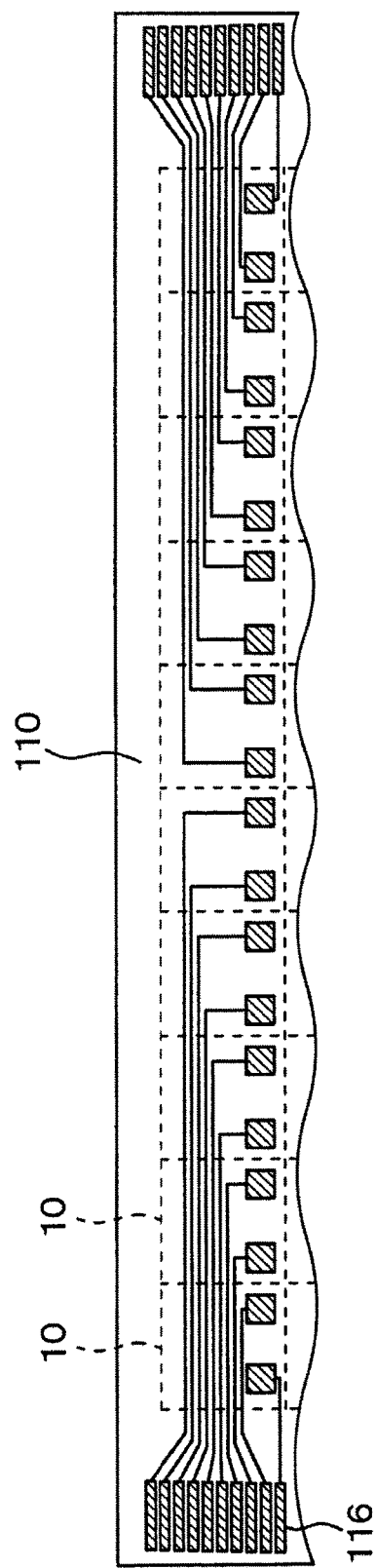
FIG. 8 is an enlarged view of the region VIII in FIG. 7.

As shown in FIGS. 7 and 8, the plurality of wiring patterns 116 extend from the respective positions of the heat flow sensor portions 10 to the end portions of the sensor module 2. As a result, two wires are formed to extend from each one of the heat flow sensor portions 10 to the end portions of the sensor module 2. Note that FIG. 7 is a plan view of the sensor module 2 from which the surface protection member 115 has been omitted. However, for easier understanding, the portions of the wiring patterns 116 which function as connection portions are hatched. As shown in FIG. 6, at the end portions of the sensor module 2, parts of the wiring patterns 116 are exposed. The exposed parts of the wiring patterns 116 form connection terminals for connecting each one of the heat flow sensor portions 10 to the electronic control unit 3.

Thus, in the present embodiment, the wiring patterns 116 connected to the individual heat flow sensor portions 10 are formed in a layer different from the layer in which the first and second interlayer connection members 130 and 140, the top-surface patterns 111, and the back-surface patterns 121 are formed (see FIG. 7). In the case of using a plurality of heat flow sensors as separate and independent bodies, when the plurality of heat flow sensors are attached to the measurement target, a space where wiring is to be placed is needed between the heat flow sensors adjacent to each other. By contrast, according to the present embodiment, a space where wiring is to be placed is not needed between the heat flow sensors adjacent to each other. This allows the plurality of heat flow sensor portions 10 to be densely arranged.

The foregoing is the basic configuration of each of the heat flow sensor portions 10 in the present embodiment. As described above, the thermoelectric conversion elements included in each one of the heat flow sensor portions 10 include the first and second interlayer connection members 130 and 140 which are embedded in the plurality of first and second via holes 101 and 102 and alternately connected in series. The first and second interlayer connection members 130 and 140 included in each one of the plurality of heat flow sensor portions 10 are formed in the same insulating base material 100.

The plurality of heat flow sensor portions 10 output respective sensor signals (electromotive forces) in accordance with the temperature difference between the both surfaces of the multilayer substrate to the electronic control unit 3. When the temperature difference between the both surfaces changes, the electromotive force generated in the first and second interlayer connection members 130 and 140 alternately connected in series changes. This allows heat flows or heat flow fluxes passing through the heat flow sensor portions 10 to be calculated from the electromotive forces generated in the heat flow sensor portions 10.

Referring to FIGS. 9A to 9H, a description will be given of a method of manufacturing the foregoing sensor module 2. FIGS. 9A to 9H show one of the heat flow sensor portions 10 and correspond to FIG. 5.

Figure 9A:
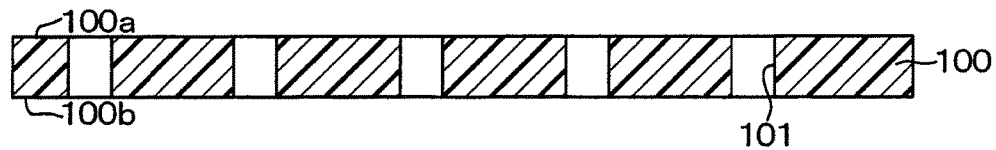
FIGS. 9A to 9H are cross-sectional views for illustrating a manufacturing process of the sensor module in the first embodiment.

First, as shown in FIG. 9A, the insulating base material 100 is prepared and the plurality of first via holes 101 are formed using a drill, a laser, or the like.

Figure 9B:
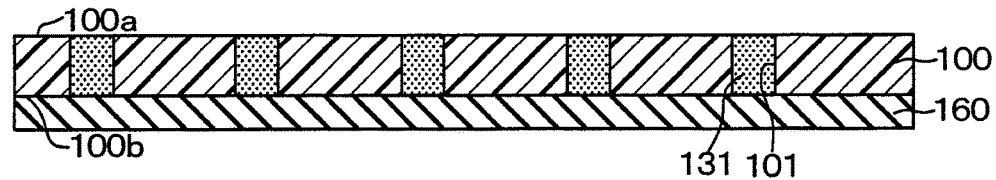

Next, as shown in FIG. 9B, each of the first via holes 101 is filled with a first conductive paste 131. Note that, as a method (device) for filling the first via holes 101 with the first conductive paste 131, the method (device) described in Japanese Patent Application No. 2010-50356 (JP 2011-187619 A) filed by the present applicant may be used appropriately.

The following is a brief description thereof. On a holder not shown, the insulating base material 100 is placed via an adsorption sheet 160 such that the back surface 100b thereof faces the adsorption sheet 160. Then, the first conductive paste 131 is melted, while the first via holes 101 are filled with the molten conductive paste 131. As a result, a major part of the organic solvent of the first conductive paste 131 is adsorbed by the adsorption sheet 160 and an alloy powder is placed in direct contact with the first via holes 101.

Note that the adsorption sheet 160 may appropriately be made of a material capable of absorbing the organic solvent of the first conductive paste 131. As the adsorption sheet 160, a typical high-quality sheet or the like is used. On the other hand, as the first conductive paste 131, a paste obtained by adding a Bi—Sb—Te alloy powder in which the metal atoms retain predetermined crystal structures to an organic solvent having a melting point of 43° C., such as paraffin, is used. Accordingly, when the first via holes 101 are filled with the first conductive paste 131, the filling is performed in the state where the top surface 100a of the insulating base material 100 is heated to about 43° C.

Figure 9C:
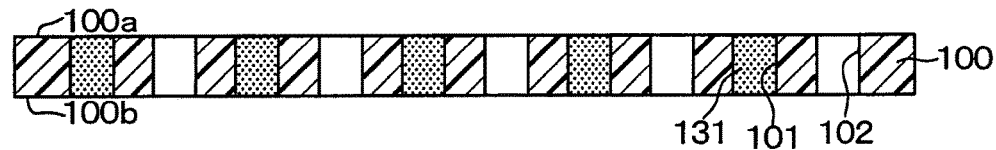

Subsequently, as shown in FIG. 9C, the plurality of second via holes 102 are formed in the insulating base material 100 using a drill, a laser, or the like. As described above, the second via holes 102 are staggered with respect to the first via holes 101 and formed so as to form a zigzag pattern in conjunction with the first via holes 101.

Figure 9D:
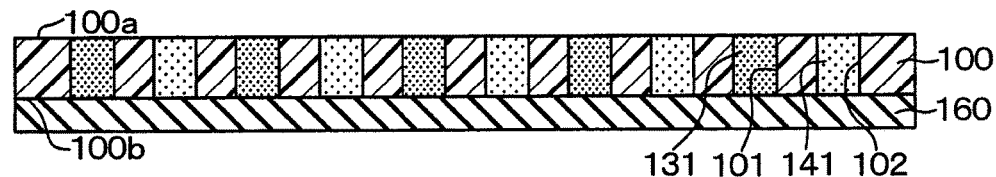

Next, as shown in FIG. 9D, each of the second via holes 102 is filled with a second conductive paste 141. Note that the step can be performed in the same step as that in FIG. 9B described above.

That is, on the holder not shown, the insulating base material 100 is placed again via the adsorption sheet 160 such that the back surface 100b thereof faces the adsorption sheet 160. Then, the second via holes 102 are filled with the second conductive paste 141. As a result, a major part of the organic solvent of the second conductive paste 141 is adsorbed by the adsorption sheet 160 and an alloy powder is placed in direct contact with the second via holes 102.

As the second conductive paste 141, a paste obtained by adding a Bi—Te alloy powder in which the metal atoms different from those included in the first conductive paste 131 retain predetermined crystal structures to an organic solvent having a melting point in the room temperature range, such as terpineol, is used. That is, as the organic solvent included in the second conductive paste 141, an organic solvent having the melting point lower than that of the organic solvent included in the first conductive paste 131 is used. When the second via holes 102 are filled with the second conductive paste 141, the filling is performed in the state where the top surface 100a of the insulating base material 100 is held at a room temperature. In other words, the filling of the second via holes 102 with the second conductive paste 141 is performed in the state where the organic solvent included in the first conductive paste 131 is solidified. This can inhibit the second conductive paste 141 from entering the first via holes 101.

Note that the state where the organic solvent included in the first conductive paste 131 is solidified is the state in which, in the step in FIG. 9B described above, the organic solvent which has not been adsorbed by the adsorption sheet 160 and has remained in the first via holes 101 is solidified.

Figure 9E:
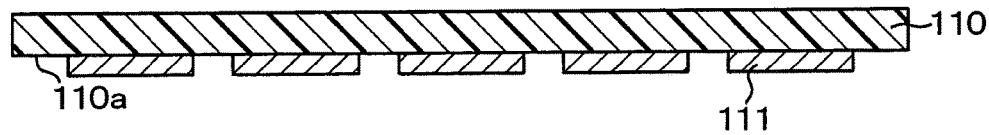
Figure 9F:
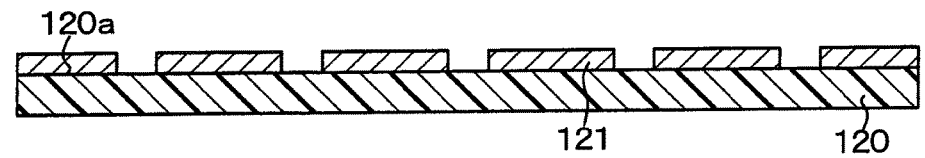

Then, in another step other than each of the foregoing steps, as shown in FIGS. 9E and 9F, on each of the one surfaces 110a and 120a of the insulating layer 110 and the back-surface protection member 120 which face the insulating base material 100, a copper foil or the like is formed. Then, by appropriately patterning the copper foil, the insulating layer 110 formed with the plurality of top-surface patterns 111 spaced apart from each other and the back-surface protection member 120 formed with the plurality of back-surface patterns 121 spaced apart from each other are prepared. As also shown in FIG. 7, the surface protection member 115 formed with the plurality of wiring patterns 116 is prepared.

Figure 9G:
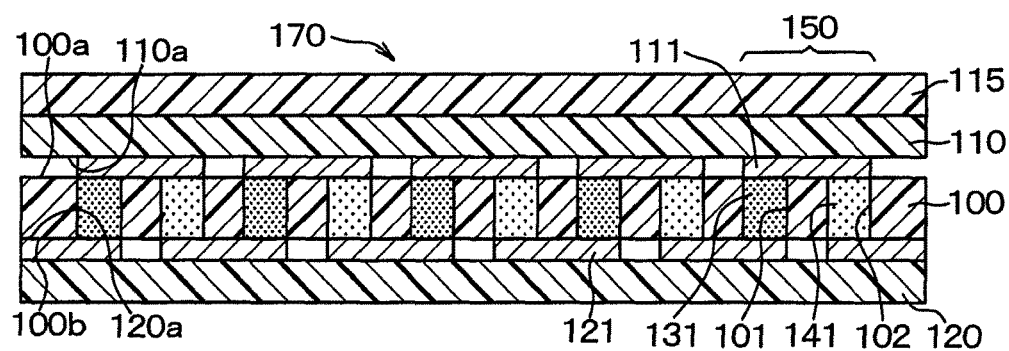

Then, as shown in FIG. 9(g), the back-surface protection member 120, the insulating base material 100, the insulating layer 110, and the surface protection member 115 are successively stacked to form a stacked body 170.

Figure 9H:
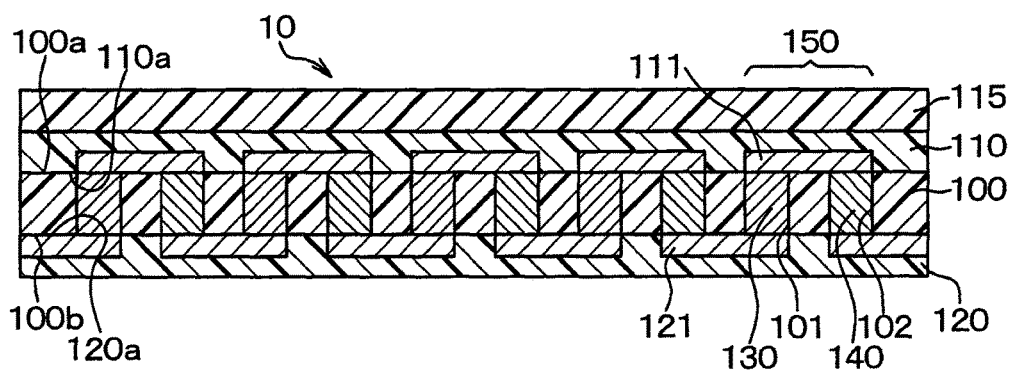

Subsequently, as shown in FIG. 9H, the stacked body 170 is disposed between a pair of pressing plates not shown. Then, a pressure is applied thereto, while the stacked body 170 is heated from the both upper and lower surfaces in the stacking direction thereof in a vacuum state, thus forming the integrated stacked body 170. Specifically, the first and second conductive pastes 131 and 141 are subjected to solid-phase sintering to form the first and second interlayer connection members 130 and 140 and the pressure is applied to the laminated body 170, while the laminated body 170 is heated such that the first and second interlayer connection members 130 and 140 are connected to the top-surface patterns 111 and the back-surface patterns 121, thus forming the integrated stacked body 170.

Note that, when the integrated stacked body 170 is formed, a shock-absorbing material such as Rockwell paper may also be placed between the stacked body 170 and the pressing plates, though the formation of the stacked body 170 is not particularly limited. In this manner, the foregoing sensor module 2 is manufactured.

Next, a description will be given of a method of measuring a heat flow distribution using the heat flow distribution measurement device 1 in the present embodiment.

As shown in FIGS. 2 and 3, the measurement target 31 is placed on the stage 23 so as to face the one surface 2a of the sensor module 2. By adjusting the height of the sensor head 21, the sensor module 2 is brought into a state in contact or non-contact with the measurement target 31.

Then, a heat flow from the measurement target 31 or a heat flow toward the measurement target 31 passes through the sensor module 2 in a direction perpendicular to the one surface 2a and the other surface 2b of the sensor module 2. As a result, the electromotive force is output from each of the heat flow sensor portions 10 to the electronic control unit 3.

Figure 10:
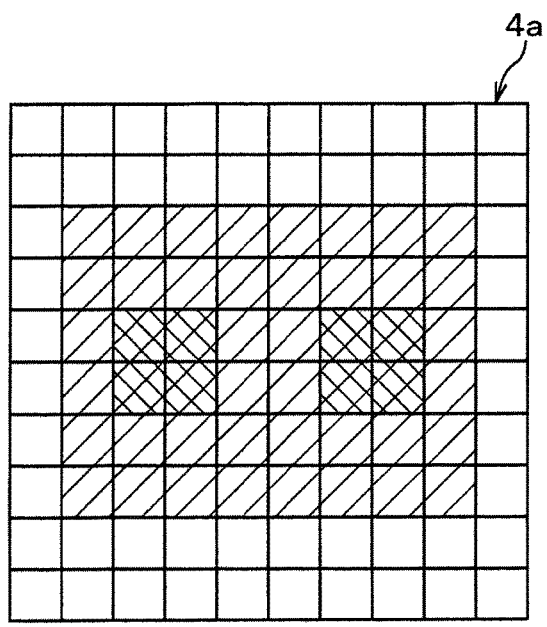
FIG. 10 is a view showing an example of a heat flow distribution image displayed on the display unit of the heat flow distribution measurement device according to the first embodiment.

The electronic control unit 3 arithmetically determines a heat flow distribution on the basis of the electromotive force from each of the heat flow sensor portions 10 to thus allow the heat flow distribution of the measurement target 31 to be obtained. The electronic control unit 3 also performs image processing and causes the display unit 4 to display a two-dimensional image of the heat flow distribution to thus allow the heat flow distribution of the measurement target 31 to be recognized as the two-dimensional image. For example, as shown in FIG. 10, a heat flow distribution image 4a showing the magnitude of the heat flow from the region corresponding to the measurement target 31 is displayed on the display unit 4. Note that, in the present embodiment, each one of the heat flow sensor portions 10 corresponds to one pixel (one of the quadrilaterals in FIG. 10) as a minimum unit of the heat flow distribution image 4a.

As has been described heretofore, the heat flow distribution measurement device 1 in the present embodiment uses the sensor module 2 having the plurality of heat flow sensor portions 10 formed in the single multilayer substrate. The thermoelectric conversion elements included in each of the heat flow sensor portions 10, i.e., the first and second interlayer connection members 130 and 140 are formed in the single multilayer substrate and are therefore manufactured by the same manufacturing process for manufacturing the multilayer substrate. Accordingly, the performance differences between the individual thermoelectric conversion elements can be reduced to be smaller than in the case where the plurality of heat flow sensors are manufactured as separate and independent bodies.

Thus, the heat flow distribution measurement device 1 in the present embodiment allows the heat flow distribution to be measured with higher precision than in the case where a heat flow distribution is measured using a plurality of heat flow sensors manufactured as separate and independent bodies.

The heat flow distribution measurement device 1 in the present embodiment allows the heat flow distribution to be measured in a state where the sensor module 2 is in contact or non-contact with the measurement target 31.

In the case of performing the measurement in a state where a plurality of heat flow sensors manufactured as separate and independent bodies are in contact with the measurement target 31, it is necessary to uniformize the states of contact of the plurality of heat flow sensors. However, when each of the plurality of heat flow sensors is manually attached to the measurement target, the state of contact varies so that it is difficult to uniformize the states of contact of the plurality of heat flow sensors.

By contrast, in the case of performing the measurement in the state where the sensor module 2 is in contact with the measurement target 31 in the present embodiment, the one sensor module 2 is brought into contact with the measurement target 31. This allows the states of contact of the individual heat flow sensor portions 10 to be uniformized.

Note that, in the present embodiment, the heat flow passing through one of the heat flow sensor portions 10 is determined and the distribution of the heat flow through the heat flow sensor portion 10 per unit area is measured as the heat flow distribution. However, as the heat flow distribution, the distribution of a heat flow flux through each one of the heat flow sensor units 10 may also be measured. Note that a heat flow is the amount of heat energy flowing per unit time and W is used as the unit thereof, while a heat flow flux is the amount of heat traversing a unit area in a unit time and $W/m^2$ is used as the unit thereof.

Second Embodiment

Figure 11:
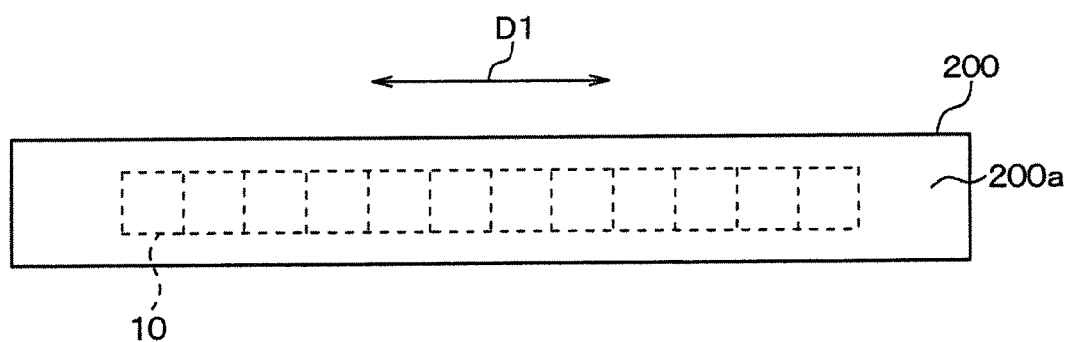
FIG. 11 is a plan view of a sensor module according to a second embodiment.

As shown in FIG. 11, in the heat flow distribution measurement device 1 of the present embodiment, the plurality of heat flow sensor portions 10 are arranged in one row in one direction D1 and a sensor module 200 having a shape elongated in the one direction D1 is used. The sensor module 200 is obtained by changing the number of the plurality of heat flow sensor portions 10 in the sensor module 2 of the first embodiment. The internal structure and the manufacturing method of the sensor module 200 are the same as those of the first embodiment. Each of the heat flow sensor portions 10 in the sensor module 200 is connected to the electronic control unit 3 via wiring in the same manner as in the first embodiment.

Figure 12:
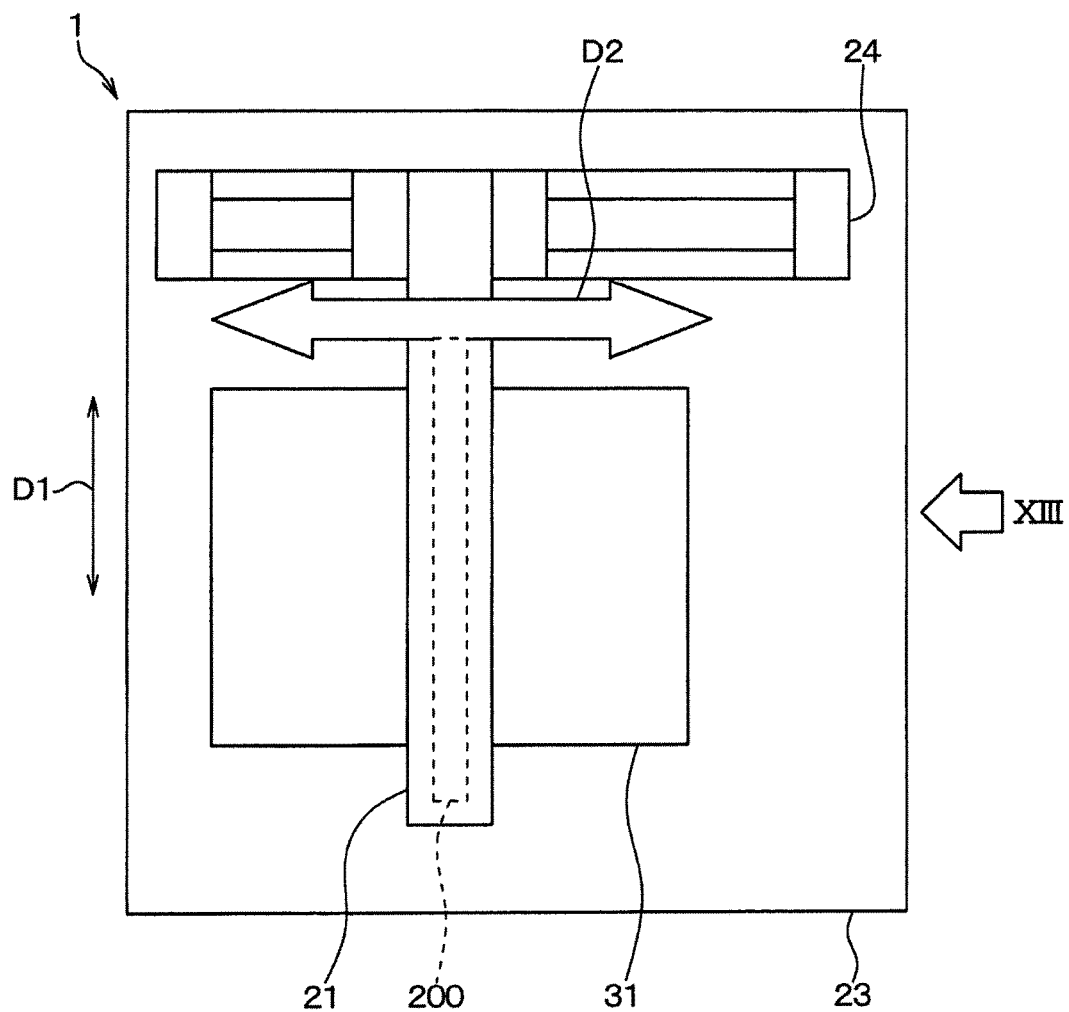
FIG. 12 is a plan view of the heat flow distribution measurement device according to the second embodiment.
Figure 13:
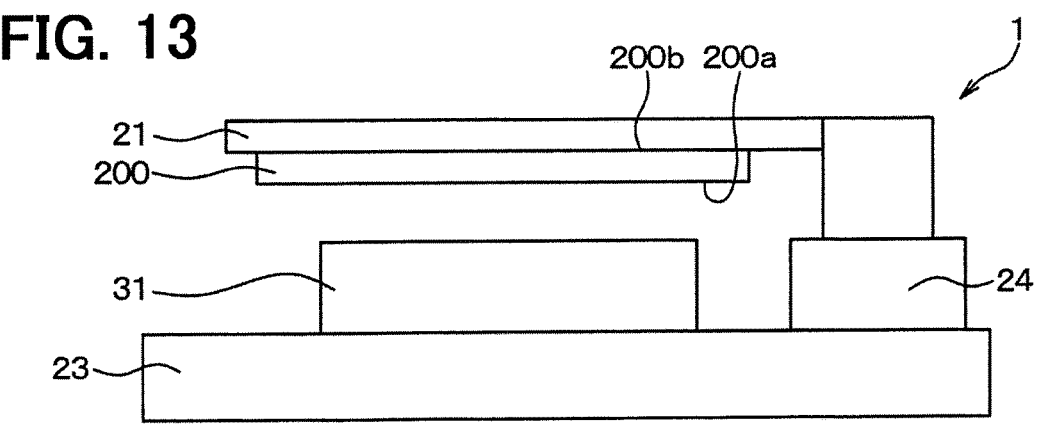
FIG. 13 is a side view of the heat flow distribution measurement device viewed in the direction shown by the arrow XIII in FIG. 12.

As shown in FIGS. 12 and 13, the heat flow distribution measurement device 1 of the present embodiment includes the sensor head 21, a uniaxial direction movement unit 24, and the stage 23.

The sensor head 21 of the present embodiment has a shape elongated in the one direction D1. The sensor module 200 is placed on the lower surface of the sensor head 21 with the longitudinal direction of the sensor head 21 coinciding with the longitudinal direction D1 of the sensor module 2. Consequently, another surface 200b of the sensor module 200 is fixed to the sensor head 21, while one surface 200a of the sensor module 200 faces the measurement target 31.

The uniaxial direction movement unit 24 is a movement unit which moves the sensor head 21 in a uniaxial direction. A movement direction D2 of the sensor head 21 is perpendicular to the longitudinal direction D1 of the sensor module 2. As the uniaxial direction movement unit 24, a movement unit having a known mechanism can be used. The movement of the uniaxial direction movement unit 24 is controlled by the electronic control unit 3. The electronic control unit 3 is adapted to be able to acquire the positional information of the sensor head 21. For example, to the uniaxial direction movement unit 24, a sensor for acquiring the positional information of the sensor head 21, which is not shown, is attached. On the basis of a sensor signal from this sensor, the electronic control unit 3 acquires the positional information of the sensor head 21.

Next, a description will be given of a method of measuring a heat flow distribution using the heat flow distribution measurement device 1 of the present embodiment.

As shown in FIGS. 12 and 13, the measurement target 31 is placed on the stage 23 so as to face the one surface 200a of the sensor module 200. By adjusting the height of the sensor head 21, the sensor module 200 is brought into a state in non-contact with the measurement target 31.

When the heat flow distribution is measured, the sensor head 21 is moved. Accordingly, the sensor module 200 moves over the surface of the measurement target 31. At this time, a heat flow from the measurement target 31 or a heat flow toward the measurement target 31 passes through the sensor module 200 in a direction perpendicular to the one surface 200a and the other surface 200b of the sensor module 200. As a result, the electromotive force generated in each of the plurality of heat flow sensor portions 10 is output to the electronic control unit 3.

Then, the electronic control unit 3 arithmetically determines a heat flow distribution on the basis of the electromotive force in each of the heat flow sensor portions 10 and the positional information of the sensor head 21 when the electromotive force is output. Thus, in the same manner as in the first embodiment, the heat flow distribution of the measurement target 31 is obtained.

Third Embodiment

Figure 14:
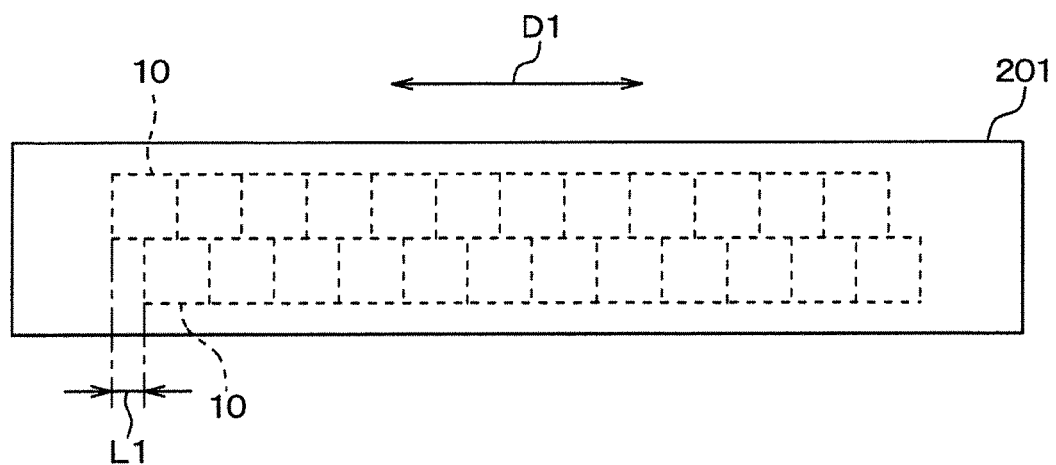
FIG. 14 is a plan view of a sensor module according to a third embodiment.

In the second embodiment, the sensor module 200 in which the plurality of heat flow sensor portions 10 are arranged in one row is used. By contrast, in the present embodiment, as shown in FIG. 14, a sensor module 201 in which the plurality of heat flow sensor portions 10 are arranged in two rows is used.

Also, in the sensor module 201, the respective positions of the heat flow sensor portions 10 in the adjacent rows which face each other are shifted from each other by a predetermined distance in the one direction D1 in which the plurality of heat flow sensor portions 10 in one row are arranged. In the present embodiment, the predetermined distance is set to a length L1 corresponding to ½ of the width of each one of the heat flow sensor portions 10.

In the present embodiment also, in the same manner as in the second embodiment, the heat flow distribution is measured while the sensor head 21 is moved in a direction perpendicular to the one direction D1.

By thus using the sensor module 201 in which the adjacent rows are placed to be shifted from each other by the predetermined distance, in the same manner as when the width of each one of the heat flow sensor portions 10 is set to the predetermined distance L1, the heat flow distribution can be measured. Thus, according to the present embodiment, the resolution of the heat flow distribution measurement can be increased without reducing the area of each one of the heat flow sensor portions 10. That is, each one of the pixels in the heat flow distribution image 4a displayed on the display unit 4 can be reduced in size.

Fourth Embodiment

Figure 15:
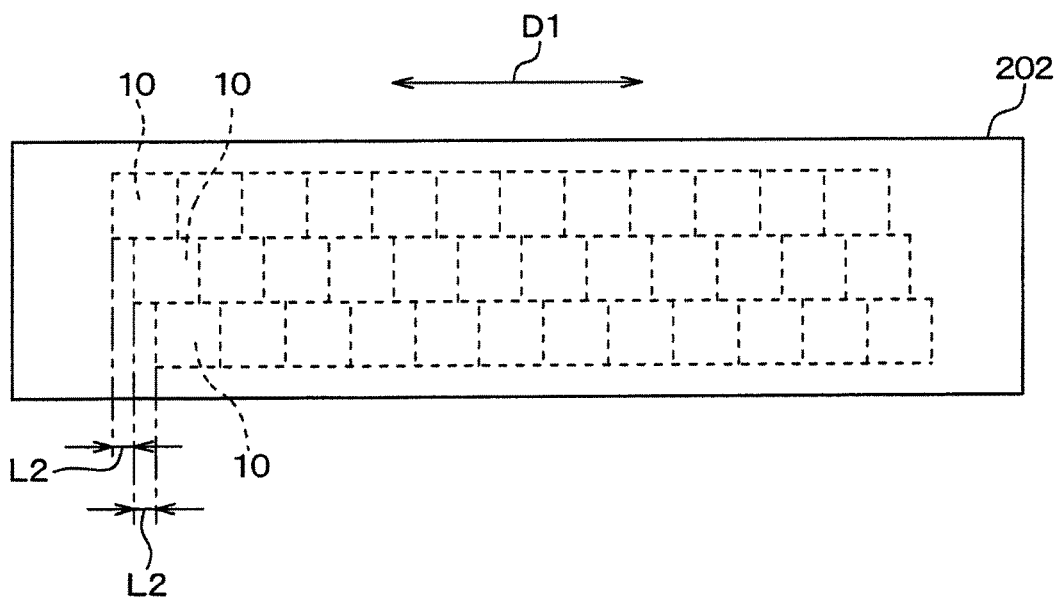
FIG. 15 is a plan view of a sensor module according to a fourth embodiment.

As shown in FIG. 15, the present embodiment uses a sensor module 202 in which the plurality of heat flow sensor portions 10 are arranged in three rows. In the sensor module 202 also, in the same manner as in the second embodiment, the adjacent rows are placed to be shifted from each other by a predetermined distance. In the present embodiment, the predetermined distance is set to a length L2 corresponding to ⅓ of the width of each one of the heat flow sensor portions 10. By thus increasing the number of the rows and reducing the predetermined distance, the resolution can further be increased.

Fifth Embodiment

Figure 16:
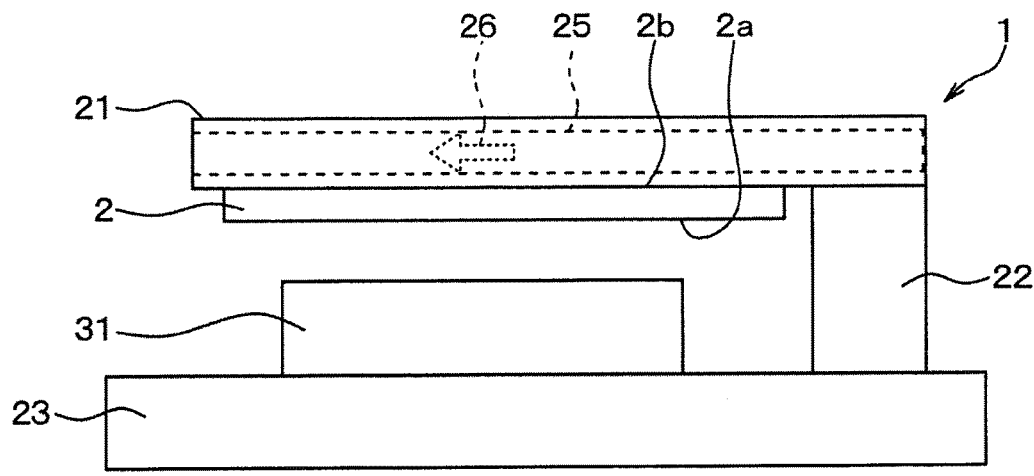
FIG. 16 is a side view of the heat flow distribution measurement device according to a fifth embodiment.

As shown in FIG. 16, the present embodiment is achieved by adding a heat medium flow path 25 to the heat flow distribution measurement device 1 in FIG. 3 described in the first embodiment.

In the present embodiment, the heat medium flow path 25 is provided in the sensor head 21. In the heat medium flow path 25, a cooling heat medium 26 which cools the sensor module 2 flows. As the cooling heat medium, a typical cooling liquid such as an antifreeze liquid can be used. In the present embodiment, the heat medium flow path 25 is connected to a heat sink, a pump, or the like not shown. Thus, a cooling liquid circulation circuit in which a cooling liquid at a predetermined temperature circulates is configured.

Differently from the present embodiment, in the case where the heat medium flow path 25 is not provided in the sensor head 21, when the heat flow distribution of the heat flow released from the measurement target 31 as a heat generator is measured, the sensor module 2 is heated by the measurement target 31 and the temperature of the sensor module 2 is increased. As a result, as time elapses, the heat flow passing through each of the heat flow sensor portions 10 changes so that the heat flow measurement value of each of the heat flow sensor portions 10 changes. That is, the heat flow measurement value of each of the heat flow sensor portions 10 drifts.

However, in the present embodiment, the heat medium flow path 25 in which the cooling heat medium 26 for cooling the sensor module 2 flows is provided in the sensor head 21, i.e., in the other surface 2b of the sensor module 2.

Accordingly, by allowing the cooling liquid to flow in the heat medium flow path 25 when the heat flow distribution of the heat flow released from the measurement target 31 as the heat generator is measured, the other surface 2b of the sensor module 2 can be cooled with the cooling liquid.

As a result, even when the sensor module 2 is heated by the measurement target 31, the temperature of the sensor module 2 can be held substantially constant and the heat flow passing through each of the heat flow sensor portions 10 can be stabilized. This can inhibit the heat flow measurement value of each of the heat flow sensor portions 10 from drifting.

Note that, in the present embodiment, it is preferable that the temperature of the sensor module 2 is measured using a temperature sensor not shown and, on the basis of the measured temperature of the sensor module 2, the electronic control unit 3 controls the flow rate of the cooling heat medium 26 flowing in the heat medium flow path 25 such that the temperature of the sensor module 2 is adjusted to be held constant.

In the present embodiment, the heat medium flow path 25 in which the cooling heat medium 26 flows is provided in the sensor head 21. However, instead of the heat medium flow path 25, another cooler such as a heat sink or a heat pipe may also be provided.

Also, in the present embodiment, the case where the measurement target 31 is the heat generator has been described. However, in the case where the measurement target 31 is a heat absorber, a heating heat medium for heating the measurement target 31 is used instead of the cooling heat medium 26. As a result, even when the sensor module 2 is cooled by the measurement target 31 in the same manner as in the present embodiment, the temperature of the sensor module 2 can be held substantially constant and the heat flow passing through each of the heat flow sensor portions 10 can be stabilized. This can inhibit the heat flow measurement value of each of the heat flow sensor portions 10 from drifting. Note that, in this case also, a heater such as an electric heater may also be provided instead of the heat medium flow path 25 in which the heating heat medium flows.

Sixth Embodiment

Figure 17:
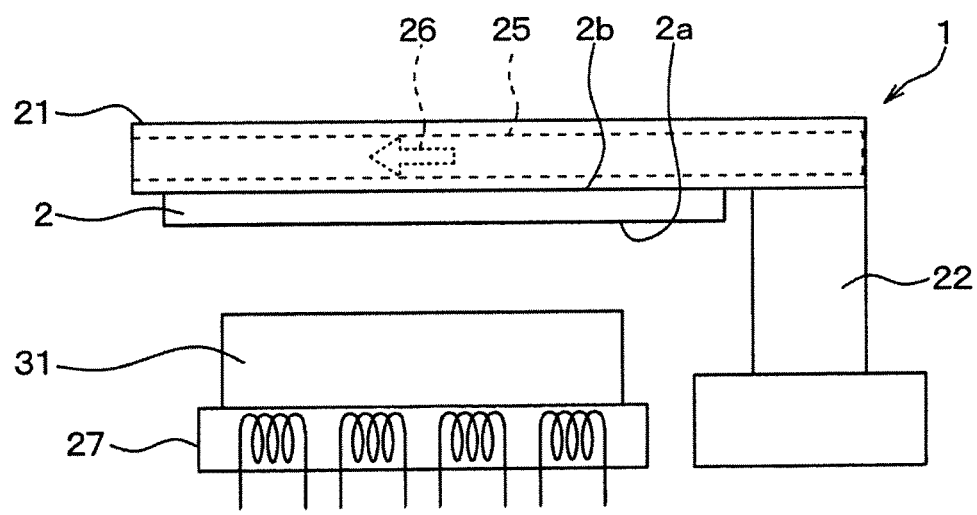
FIG. 17 is a side view of the heat flow distribution measurement device according to a sixth embodiment.

As shown in FIG. 17, the present embodiment has been achieved by replacing the stage 23 in the heat flow distribution measurement device 1 in FIG. 16 described in the fifth embodiment with a heater 27.

In the present embodiment, on the surface of the measurement target 31 which is opposite to the surface thereof closer to the sensor module 2, the heater 27 is disposed. The heater 27 is for heating the measurement target 31 and is formed of an electric heater or the like.

In the measurement of the heat flow distribution using the heat flow distribution measurement device 1, the measurement is performed in the same manner as in the fifth embodiment in the state in which the measurement target 31 is heated using the heater 27.

According to the present embodiment, the heat flow distribution of the heat flow released from the heater 27 and passing through the measurement target 31 can be measured. Consequently, it is possible to precisely measure the distribution of the heat insulating property of the measurement target 31 and evaluate the heat insulating performance of the measurement target 31.

Other Embodiments

The present disclosure is not limited to the embodiment described above, but can be changed appropriately as follows.

(1) In each of the embodiments described above, the heat flow is calculated on the basis of the electromotive force (voltage value) generated in each of the heat flow sensor portions. However, the calculation may also be performed on the basis of a current value instead of the voltage value. Briefly, the heat flow can be calculated on the basis of an electric output such as the voltage or current generated in the heat flow sensor portion.

(2) In each of the embodiments described above, the respective metals forming the first and second interlayer connection members 130 and 140 are the Bi—Sb—Te alloy and the Bi—Te alloy. However, the metal forming each of the first and second interlayer connection members 130 and 140 may also be another alloy. In each of the embodiments described above, each of the metals forming the first and second interlayer connection members 130 and 140 is a sintered alloy resulting from solid-phase sintering. However, it is appropriate that at least one of the metals forming the first and second interlayer connection members 130 and 140 is a sintered alloy resulting from solid-phase sintering. As a result, the electromotive force can be set larger than in the case where neither of the metals forming the first and second interlayer connection members 130 and 140 is a sintered metal resulting from solid-phase sintering.

(3) In each of the embodiments described above, the multilayer substrate included in the sensor module includes the plurality of stacked insulating layers each formed of a thermoplastic resin. However, the multilayer substrate may also include a plurality of stacked insulating layers each made of a material other than a thermoplastic resin. Examples of the material of the insulating layers which is other than a thermoplastic resin include a thermosetting resin.

(4) In each of the embodiments described above, the multilayer substrate has the configuration in which the insulating base material 100, the insulating layer 110, the top-surface protection member 115, and the back-surface protection member 120 are stacked. However, the multilayer substrate may also have another configuration as long as a plurality of insulating layers are stacked therein. That is, the multilayer substrate may appropriately have the insulating base material 100 formed with the plurality of through holes 101 and 102 as one of the plurality of insulating layers. The number of the insulating layers located on both sides of the insulating base material 100 can arbitrarily be changed.

(5) In the first embodiment, it has been described that the electromotive force is output from each of the heat flow sensor portions 10 as a result of the passing of the heat flow through the sensor module 2 in a direction perpendicular to the one surface 2a and the other surface 2b of the sensor module 2. However, the outputting of the electromotive force from each of the heat flow sensor portions 10 is not limited to the case where the heat flow passes through the sensor module 2 in a direction perpendicular to the one surface 2a and the other surface 2b of the sensor module 2. In the case where the heat flow passes through the sensor module 2 in a direction extending from one of the one surface 2a and the other surface 2b of the sensor module 2 to the other thereof, an electromotive force is output from each of the heat flow sensor portions 10. The same holds true in each of the embodiments described above which are other than the first embodiment. For example, in the second embodiment also, in the case where the heat flow passes through the sensor module 200 in a direction extending from one of the one surface 200a and the other surface 200b of the sensor module 200 to the other thereof, an electromotive force is output from each of the heat flow sensor portions 10.

(6) In the sensor module 2 in the first embodiment, the plurality of heat flow sensor portions 10 are arranged in a matrix configuration in the directions parallel with the one surface 2a. However, the directions in which the plurality of heat flow sensor portions 10 are arranged may also be directions oblique to the one surface 2a, not directions completely parallel with the one surface 2a. Briefly, the plurality of heat flow sensor portions 10 may appropriately be arranged in directions along the one surface 2a. Note that the directions along the one surface 2a include a direction completely parallel with the one surface 2a and a direction approximately parallel with the one surface 2a. The same also holds true in the sensor modules 200, 201, 202, and the like in the second to fourth embodiments.

(7) In the second to fourth embodiments, the moving direction of the uniaxial direction movement unit 24 is perpendicular to the one direction D1 in which the plurality of heat flow sensor portions 10 are arranged. However, the moving direction of the uniaxial direction movement unit 24 need not be perpendicular to the one direction D1. The moving direction of the uniaxial direction movement unit 24 may appropriately be a direction intersecting the one direction D1.

(8) The individual embodiments described above are by no means irrelevant to each other and can appropriately be combined unless a combination thereof is obviously unacceptable. Also, it goes without saying that, in each of the embodiments described above, the components thereof are not necessarily indispensable unless it is particularly clearly stated that the components of the embodiment are indispensable or unless the components of the embodiment can be considered to be obviously indispensable in principle.

It is understood that the present disclosure has been described in accordance with the embodiments, but the present disclosure is not limited to the embodiments and the structures thereof. The present disclosure also encompasses variations in the equivalent range as various modifications. In addition, various combinations and embodiments, and further, only one element thereof, less or more, and the form and other combinations including, are intended to fall within the spirit and scope of the present disclosure.

The invention claimed is:

1. A heat flow distribution measurement device comprising:
 a sensor module including one multilayer substrate and a plurality of heat flow sensor portions, the multilayer substrate having one surface and another surface opposite to the one surface and having a plurality of stacked insulating layers each formed of a thermoplastic resin, the plurality of heat flow sensor portions being arranged inside of the multilayer substrate,
 wherein the plurality of heat flow sensor portions are individually provided by a plurality of electrically independent thermoelectric conversion elements and, when the sensor module is placed with the one surface facing a measurement target of which a heat flow distribution is to be measured, each of the electrically independent thermoelectric conversion elements produces an electric output in accordance with a heat flow passing through the inside of the multilayer substrate in a direction perpendicular to the one surface,
 wherein the multilayer substrate has, as the plurality of stacked insulating layers, an insulating base material formed with a plurality of through holes, an insulating layer adjacent to a first surface of the insulating base material, a back-surface protection member adjacent to a second surface of the insulating base material opposite to the insulating layer,
 wherein the multilayer substrate further has a top-surface protection member adjacent to the insulating layer opposite to the back-surface protection member, and a plurality of wiring patterns adjacent to the top-surface protection member,
 wherein the multilayer substrate further has first and second conductors formed of different conductors and embedded in the plurality of through holes of the insulating base material,
 wherein each of the electrically independent thermoelectric conversion elements is provided by the first and second conductors alternately connected in series,
 wherein the first and second conductors providing the electrically independent thermoelectric conversion elements are formed in the same insulating base material, and
 wherein the wiring patterns are independently connected to ends of the respective electrically independent thermoelectric conversion elements through interlayer connection members and are extended to end portions of the sensor module.

2. The heat flow distribution measurement device according to claim 1, further comprising:
 an arithmetic portion that arithmetically determines the heat flow distribution on the basis of the output produced by each of the plurality of heat flow sensor portions.

3. The heat flow distribution measurement device according to claim 2,
 wherein, in a direction parallel with the one surface, the plurality of heat flow sensor portions are aligned in one row or a plurality of rows in one direction,
 the heat flow distribution measurement device further comprising:
 a movement unit that moves the sensor module in a direction perpendicular to the one direction,
 wherein the arithmetic portion arithmetically determines the heat flow distribution on the basis of the output produced by each of the plurality of heat flow sensor portions when the sensor module is moved and a position of the sensor module when the output is produced.

4. The heat flow distribution measurement device according to claim 3,
 wherein the plurality of heat flow sensor portions are aligned in the plurality of rows in the one direction and the heat flow sensor portions in adjacent rows which face each other are shifted from each other by a predetermined distance in the one direction.

5. The heat flow distribution measurement device according to claim 1,
 wherein, in directions parallel with the one surface, the plurality of heat flow sensor portions are arranged in a matrix configuration.

6. The heat flow distribution measurement device according to claim 1, further comprising:
 a cooler or a heater provided on the another surface of the sensor module to cool or heat the sensor module.

7. A heat flow distribution measurement device comprising:

a sensor module including one multilayer substrate and a plurality of heat flow sensor portions, the multilayer substrate having one surface and another surface opposite to the one surface and having a plurality of stacked insulating layers, the plurality of heat flow sensor portions being arranged inside of the multilayer substrate, wherein the plurality of heat flow sensor portions are individually provided by a plurality of electrically independent thermoelectric conversion elements and, when the sensor module is placed with the one surface facing a measurement target of which a heat flow distribution is to be measured, each of the electrically independent thermoelectric conversion elements produces an electric output in accordance with a heat flow passing through the inside of the multilayer substrate in a direction extending from one of the one surface and the another surface to the other of the one surface and the another surface, wherein the multilayer substrate has, as the plurality of stacked insulating layers, an insulating base material formed with a plurality of through holes, an insulating layer adjacent to a first surface of the insulating base material, a back-surface protection member adjacent to a second surface of the insulating base material opposite to the insulating layer, wherein the multilayer substrate further has a top-surface protection member adjacent to the insulating layer opposite to the back-surface protection member, and a plurality of wiring patterns adjacent to the top-surface protection member, wherein the multilayer substrate further has first and second conductors formed of different conductors and embedded in the plurality of through holes of the insulating base material, wherein each of the electrically independent thermoelectric conversion elements is provided by the first and second conductors alternately connected in series, wherein the first and second conductors providing the electrically independent thermoelectric conversion elements are formed in the same insulating base material, and wherein the wiring patterns are independently connected to ends of the respective electrically independent thermoelectric conversion elements through interlayer connection members and are extended to end portions of the sensor module.

8. The heat flow distribution measurement device according to claim 7, further comprising:
an arithmetic portion that arithmetically determines the heat flow distribution on the basis of the output produced by each of the plurality of heat flow sensor portions.

9. The heat flow distribution measurement device according to claim 8,
wherein, in a direction along the one surface, the plurality of heat flow sensor portions are aligned in one row or a plurality of rows in one direction,
the heat flow distribution measurement device further comprising:
a movement unit that moves the sensor module in a direction intersecting the one direction,
wherein the arithmetic portion arithmetically determines the heat flow distribution on the basis of the output produced by each of the plurality of heat flow sensor portions when the sensor module is moved and a position of the sensor module when the output is produced.

10. The heat flow distribution measurement device according to claim 7,
wherein, in directions along the one surface, the plurality of heat flow sensor portions are arranged in a matrix configuration.

* * * * *